(12) United States Patent
Jungles

(10) Patent No.: US 10,463,835 B2
(45) Date of Patent: *Nov. 5, 2019

(54) DISTAL WIRE SECUREMENT IN STEERABLE CATHETER

(71) Applicant: Cook Medical Technolgoies LLC, Bloomington, IN (US)

(72) Inventor: Luke T. Jungles, Winston-Salem, NC (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 257 days.

This patent is subject to a terminal disclaimer.

(21) Appl. No.: 15/655,037

(22) Filed: Jul. 20, 2017

(65) Prior Publication Data

US 2018/0028786 A1 Feb. 1, 2018

Related U.S. Application Data

(60) Provisional application No. 62/367,951, filed on Jul. 28, 2016.

(51) Int. Cl.
*A61M 25/01* (2006.01)
*A61B 18/24* (2006.01)
*A61M 25/10* (2013.01)

(52) U.S. Cl.
CPC ......... *A61M 25/0147* (2013.01); *A61B 18/24* (2013.01); *A61M 25/0136* (2013.01); *A61M 25/0144* (2013.01); *A61M 2025/1084* (2013.01)

(58) Field of Classification Search
CPC ............ A61M 25/0067; A61M 25/007; A61M 25/09033; A61M 2025/0186; A61M 25/09175; A61M 25/0147; A61M 25/0144; A61M 25/0136; A61M 2025/1084; A61M 2025/015; A61M 25/0029; A61B 18/24; A61B 1/0057; A61B 1/0052;
(Continued)

(56) References Cited

U.S. PATENT DOCUMENTS

| 4,911,148 A | 3/1990 | Sosnowski et al. |
| 5,448,989 A | 9/1995 | Heckele |
| 5,752,912 A | 5/1998 | Takahashi et al. |

(Continued)

FOREIGN PATENT DOCUMENTS

| EP | 0790066 | 4/2000 |
| EP | 1457244 | 9/2004 |

*Primary Examiner* — Amber R Stiles
(74) *Attorney, Agent, or Firm* — Brinks Gilson & Lione

(57) ABSTRACT

A secure attachment method and structure for a wire (including non-metallic fiber, yarn, cable, etc.) is provided within a steerable catheter that includes a proximal end, a distal end, and an intermediate catheter body length therebetween, with at least a first catheter lumen extending longitudinally through the catheter body, at least a first elongate wire disposed longitudinally through the first catheter lumen, and a first adhesive having a first viscosity, the first adhesive disposed substantially within, and securing the wire to, the first longitudinal catheter lumen, where at least a lengthwise portion of the wire is frayed or otherwise at least partially disaggregated. The structure and method provides for robustly secure affixation that will allow steering/deflection control by manipulation of another portion of the wire.

20 Claims, 12 Drawing Sheets

(58) Field of Classification Search
CPC ........ A61B 1/0011; A61B 2017/00296; A61B 2017/00323; A61B 17/00234
See application file for complete search history.

(56) References Cited

U.S. PATENT DOCUMENTS

| | | |
|---|---|---|
| 7,553,305 B2 | 6/2009 | Honebrink et al. |
| 7,736,303 B2 | 6/2010 | Miyagi et al. |
| 7,998,112 B2 | 8/2011 | Chow et al. |
| 8,083,879 B2 | 12/2011 | Swinehart et al. |
| 8,540,696 B2 | 9/2013 | McDaniel et al. |
| 9,138,131 B2 | 9/2015 | Sato |
| 2001/0025134 A1 | 9/2001 | Bon et al. |
| 2007/0129605 A1* | 6/2007 | Schaaf .............. A61B 1/00082 600/146 |
| 2007/0156115 A1 | 7/2007 | Hosoi et al. |
| 2015/0297346 A1 | 10/2015 | Duffy et al. |
| 2018/0028784 A1* | 2/2018 | Jungles ............ A61M 25/0026 |

* cited by examiner

DISTAL WIRE SECUREMENT IN STEERABLE CATHETER

CROSS-REFERENCE TO RELATED APPLICATIONS

This application is a non-provisional application which claims priority to U.S. provisional application Ser. No. 62/367,951; filed Jul. 28, 2016, which is incorporated by reference herein in its entirety.

TECHNICAL FIELD

Embodiments disclosed herein generally relate to steerable catheters, including endoscopes. More particularly embodiments disclosed herein relate to a structures and methods for securely attaching the control wires/fibers within a steerable catheter.

BACKGROUND

Deflecting catheters, also referred to as steerable catheters are used in a variety of medical and non-medical procedures. In diagnostic and therapeutic medical procedures, a steerable catheter provides an operator (e.g., physician) with the ability to articulate the distal tip of the catheter in order to travel through constrained and/or tortuous anatomy, and/or to direct the distal catheter tip in a particular direction. Similar mechanisms are used in medical and nonmedical endoscopes to steer them to a target site and to orient a device portion (e.g., including a camera or other visualization means) in a desired direction.

In a typical design, control wires are manipulably attached at a proximal end of the device, and also attached at or near a distal end of the device. Such a configuration operates by manipulating one or more of the control wires to increase and/or decrease a generally longitudinal force on the distal device end that will deflect it in a desired direction. In order to prevent a premature or undesired deflection of the device, it is necessary to provide a balanced starting tension between the proximal and distal ends of the control wires. Various mechanisms in the art have been developed for doing this including threaded tensioning bolts or pins that include an aperture transversely through a head and/or shaft for receiving a proximal end portion of one or more control wires, which can then be tightened or loosened in order to provide a desired tensioning level of the control wire(s). These mechanisms often are mounted to a shaft or housing of the steerable device.

It is be desirable to provide tensioning means that provide finely tunable tensioning for very small diameter fibers, where the tuned/tensioned fibers will be secure in order to provide predictable and desirable steering behavior for a steerable catheter, and particularly for a steerable cholangioscope or other small-diameter endoscope, including providing highly-secure proximal-end anchoring of the fibers to/within the control handle.

BRIEF SUMMARY

In one aspect, embodiments disclosed herein may include a steerable catheter device with steering control wires fixedly attached in a distal end of a catheter shaft, as well as methods for effecting that fixed attachment.

In one aspect, embodiments disclosed herein may include a secure attachment of a wire within a steerable catheter that includes a proximal end, a distal end, and an intermediate catheter body length therebetween, with at least a first catheter lumen extending longitudinally through the catheter body, at least a first elongate wire disposed longitudinally through the first catheter lumen, and a first adhesive having a first viscosity, the first adhesive disposed substantially within, and securing the wire to, the first longitudinal lumen, where at least a lengthwise portion of the wire is frayed or otherwise at least partially disaggregated.

DETAILED DESCRIPTION

Figure 1:
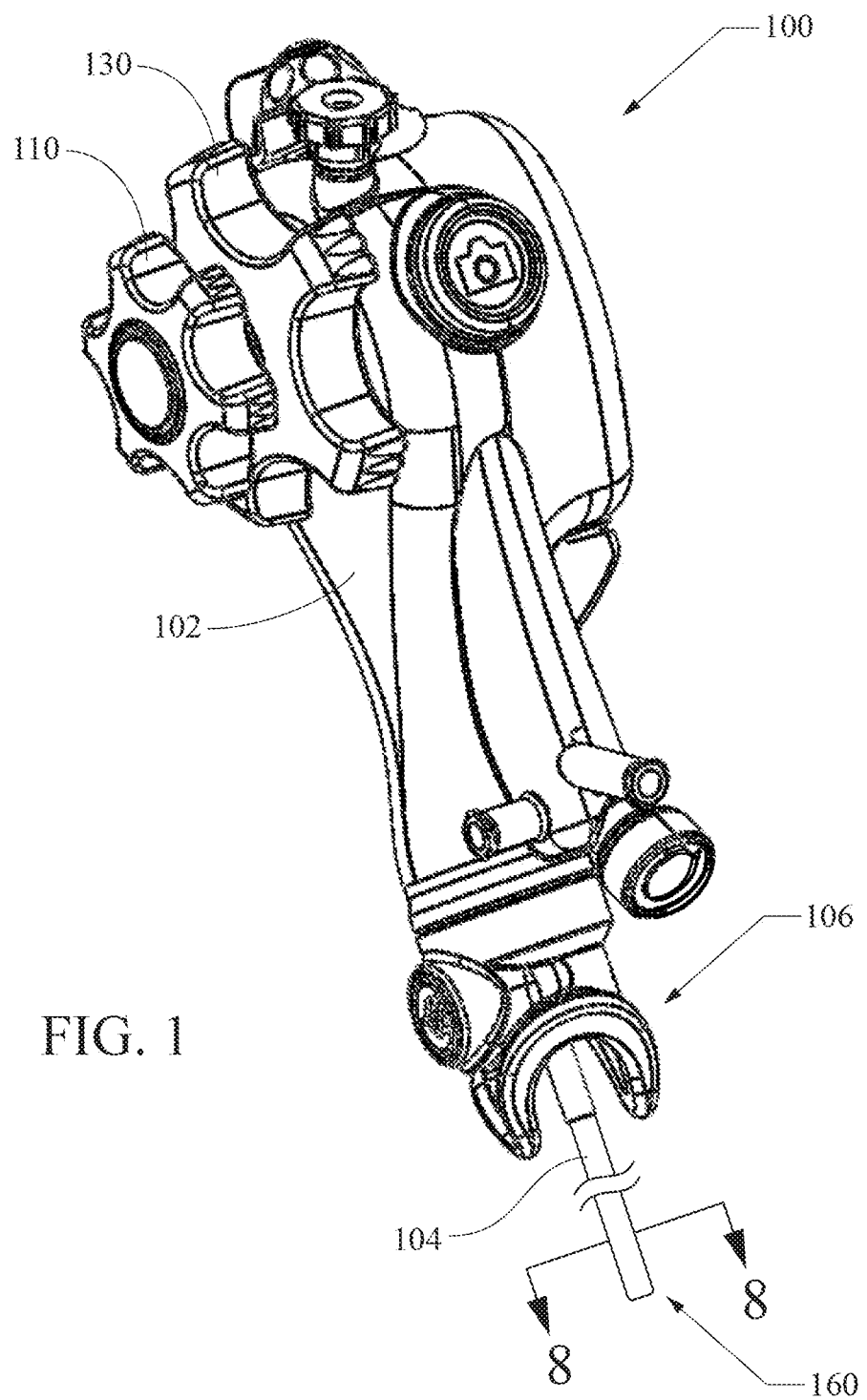
FIG. 1 shows a steerable catheter device embodiment.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

Generally, embodiments disclosed herein relate to a structure and system for securely attaching the proximal ends of control wires (including any kind of control fiber, regardless of construction material) to the control spool(s) of a steerable catheter. In the most preferred embodiments, the structure and system include means for tuning—that is finely adjusting—relative tension of each of those control wires between the proximal end and a permanently/securely attached distal control wire end attached more distally within the steerable device. Too much or too little tension in each of the control wires (on its own, and more particularly in relation to the other control wire(s)) can cause premature or otherwise undesired deflection of the steerable device and/or may cause the steerable device to operate in a manner that is not desired or predictable. During assembly of a steerable catheter device, the system can be used to take up slackness one or all control wires.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

The terms "proximal" and "distal" are used herein in the common usage sense where they refer respectively to a handle/doctor-end of a device or related object and a tool/patient-end of a device or related object. The term "about," "substantially," and other relative terms and terms of degree, when used with reference to any volume, dimension, proportion, or other quantitative value is intended to communicate a definite and identifiable value within the standard parameters that would be understood by one of skill in the art, and should be interpreted to include at least any legal equivalents, minor but functionally-insignificant variants, and encompassing a range that includes up to a range mathematically significant figures, although not requiring the full breadth of such range.

The term "control wire" (including just "wire") is used herein to denote the elongate members that connect a control surface of a steerable catheter with a deflectable distal portion of the catheter, and it may include metallic, polymeric, and/or other materials including—by way of non-limiting example—ultrahigh molecular weight polyethylene yarn (e.g., Dyneema™), aramid fibers, monofilament line, multifilament/multifilar cable, and/or other materials that preferably have high tensile strength with low longitudinal stretch so as to provide predictable operation behavior. With regard to distal attachment of the control wire(s), a multifilar, braided, or other structure is preferred, which may be at least partially frayed or otherwise partially disaggregated (e.g., in order to provide greater surface area than a unitary aggregated wire structure, as described further below). One example of a control wire may include a 4×-50 Denier ultra-high tenacity polyethylene braid having a very small outer diameter of about 0.18 mm (measured in accordance with ASTM D-1907); high strength (about 5.6 kg, and at least equal to or greater than 4.75 kg, measured in accordance with ASTM D-6775); low longitudinal stretch/elongation (about 5%, ±2%, measured in accordance with ASTM D-6775) (e.g., as available from Textile Development Associates Inc. of Brookfield, Conn.). Certain preferred control wire embodiments include or may even consist of high modulus fiber material that is nonconductive and/or substantially nonstretching. In one embodiment, a high modulus fiber control wire material may be braided. One such high modulus fiber material can be a High Molecular Density Polyethylene, a melt spun liquid crystal polymer fiber rope, or a spun para-aramid fiber polymer, or a high strength ceramic fiber. In some embodiments, a high modulus fiber control wire material may have a tensile strength in a range of about 300 ksi (2,000 MPa) to 1,500 ksi (10,400 MPa), and/or a tensile modulus in the range of about 5,000 ksi (35,000 MPa) to about 20,000 ksi (140,000 MPa).

One embodiment of a steerable catheter device 100 is described with reference to FIG. 1. The steerable catheter device 100 includes a proximal control handle body 102 with a steerable catheter body 104 extending distally therefrom. Various embodiments may include one or more different steering control means known in the art. This illustrated embodiment includes a pair of control wheels, with an outer control wheel 110 and an inner control wheel 130. As set forth in greater detail below, the outer control wheel 110 is disposed in mechanical communication with a pair of control wires that are operable, upon wheel rotation, to deflect the catheter body 104 along a first plane, and the inner control wheel 130 is disposed in mechanical communication with another pair of control wires that are operable, upon wheel rotation, to deflect the catheter body 104 along a second plane that may be generally orthogonal to the first plane. Simultaneous or sequential operation of the outer and inner wheels 110, 130 preferably can deflect the distal end portion 160 of the catheter body 104 in any direction around a 360-degree circle defined generally by a circumference of the catheter. This embodiment also shows a mounting structure 106 that may be used to mount the steerable catheter 100 to another device (e.g., an endoscope, or other piece of equipment). Steering mechanisms using control wires are well-known in the art including in U.S. Pat. Pub. No. 2015/0366435 to Williams, which is incorporated herein by reference in its entirety. The overall control structure described is also well known in the steerable device art, including particularly the endoscope art, but those devices lack the currently disclosed finely-controlled mechanism for efficient and effective tensioning of control wires. Certain embodiments in keeping with the present disclosure may include at least one visualization element (as well as supporting hardware and/or software, not shown—but well-known in the art and readily understandable as using electrical and/or optical devices such as CCD, fiber optic, CMOS, etc.) for use of such embodiments as endoscopic devices including, for example, as a cholangioscope configured for use with and through a larger endoscope.

Figure 2:
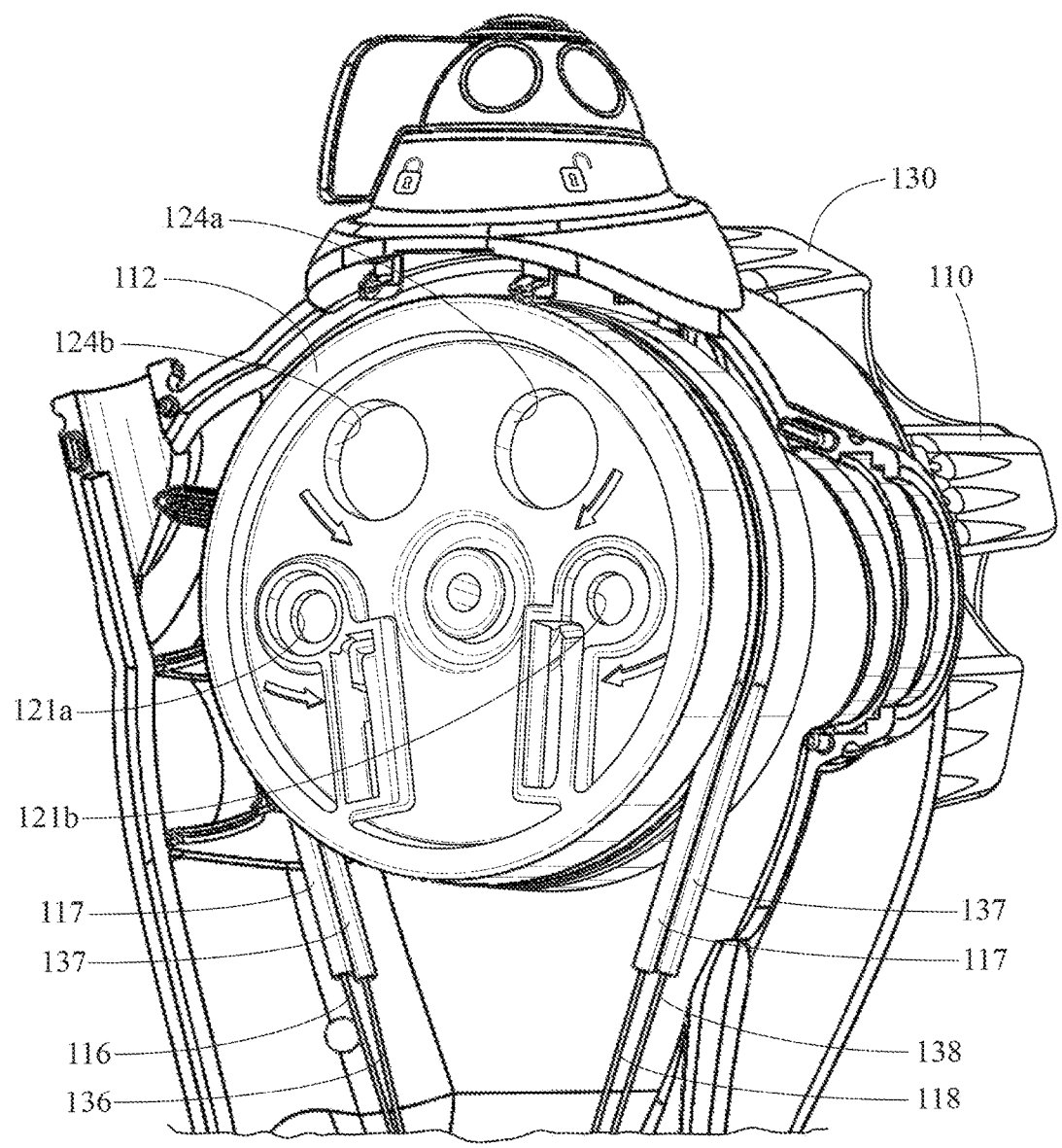
FIG. 2 is a partially disassembled perspective view of the embodiment of FIG. 1.
Figure 3:
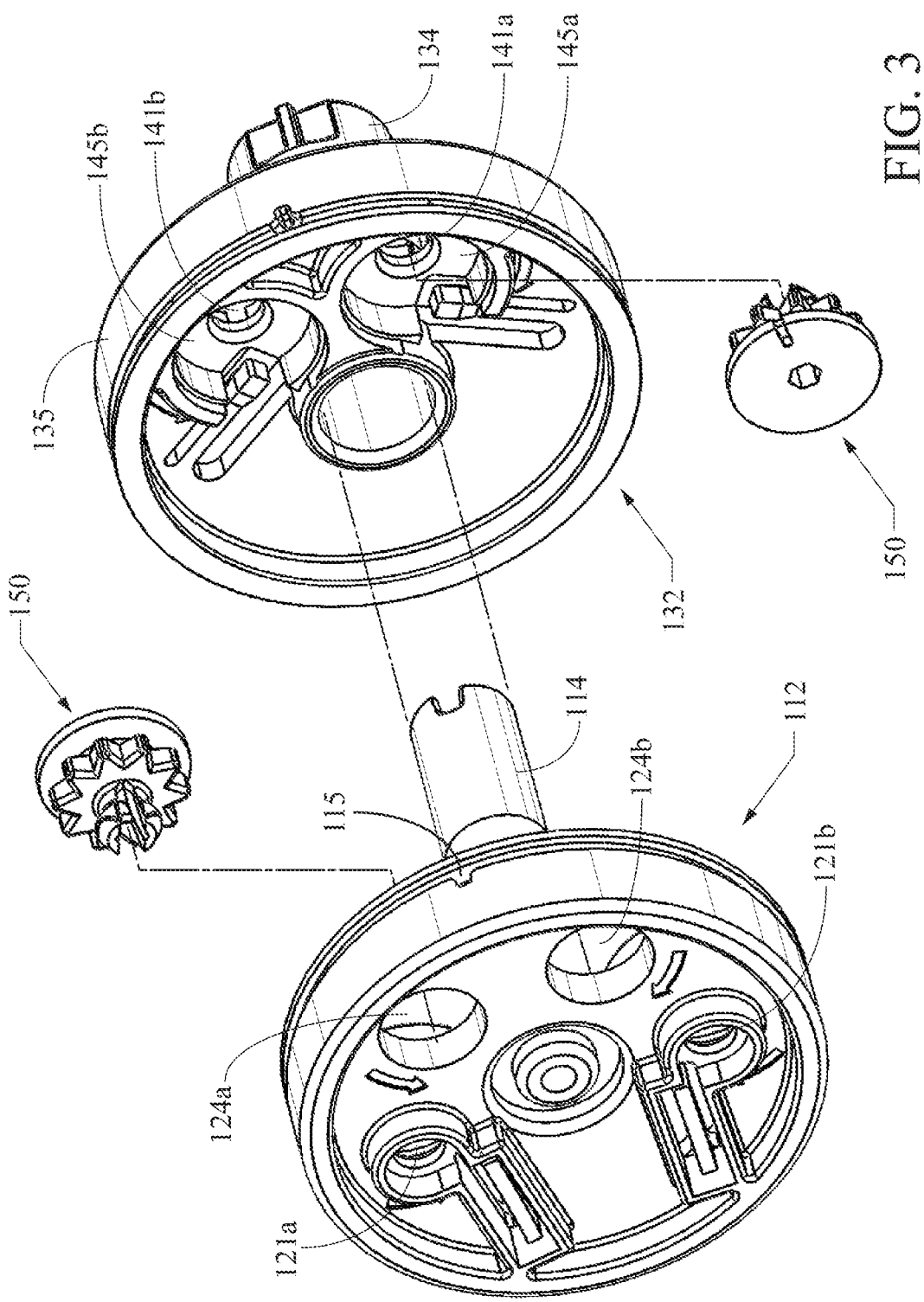
FIG. 3 shows inner and outer spools with two exemplary (of four total) control-wire winding gears.
Figure 7B:
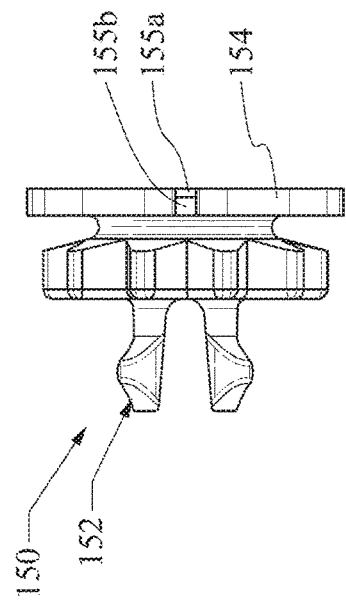
FIGS. 7A-7D show four different views of a control-wire winding gear.
Figure 7A:
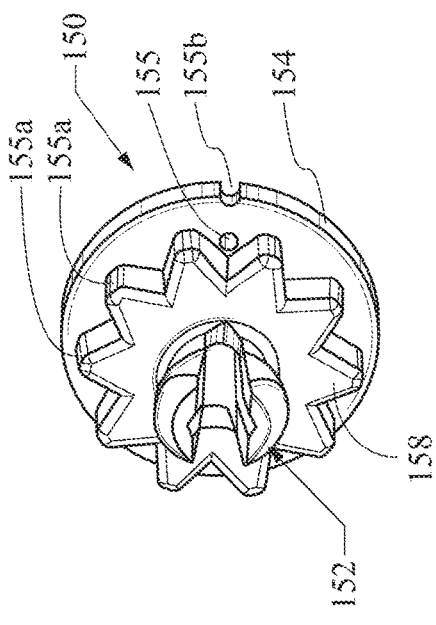
Figure 7D:
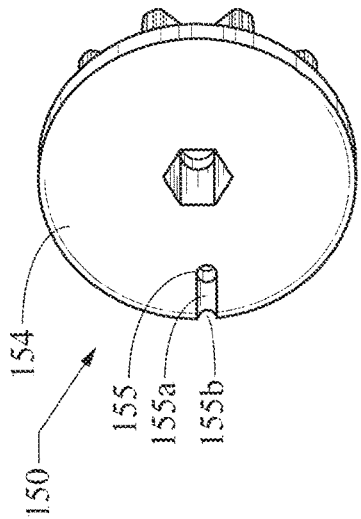
Figure 7C:
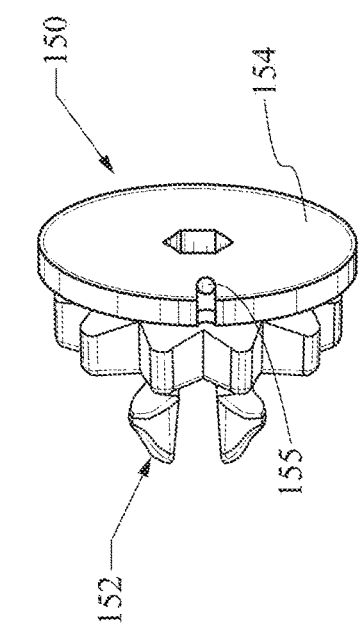
Figure 7E:
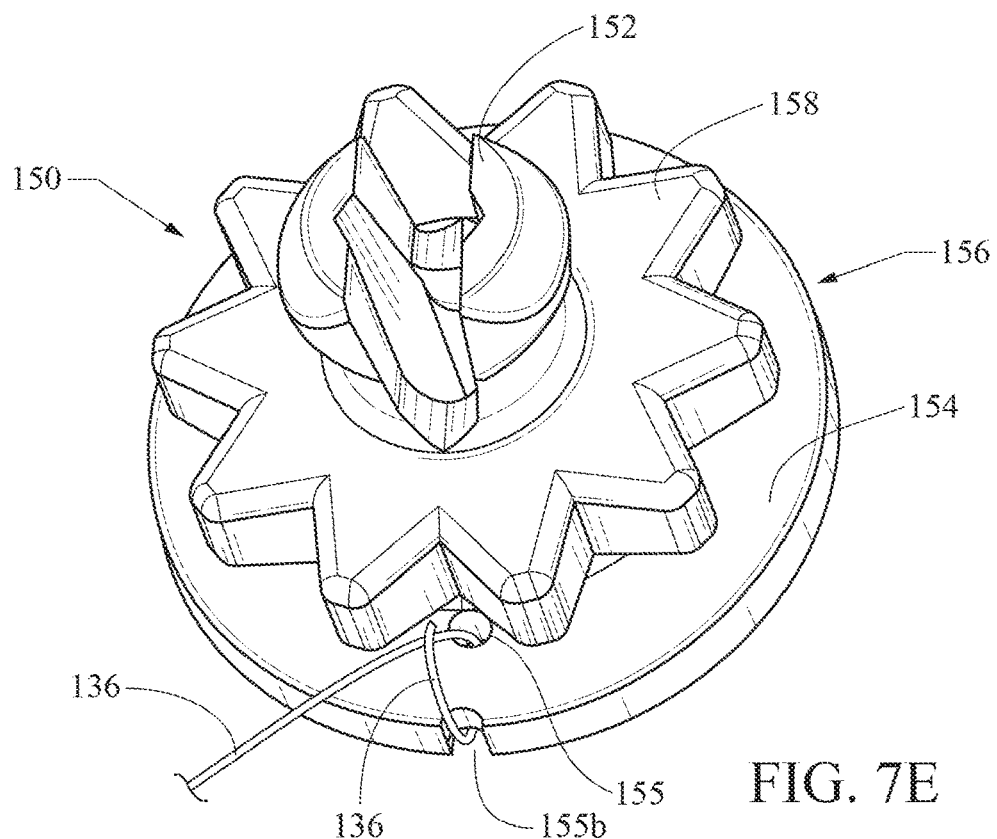
FIGS. 7E-7F show opposed sides of the control-wire winding gear, for illustration of engaging with a control wire.
Figure 7F:
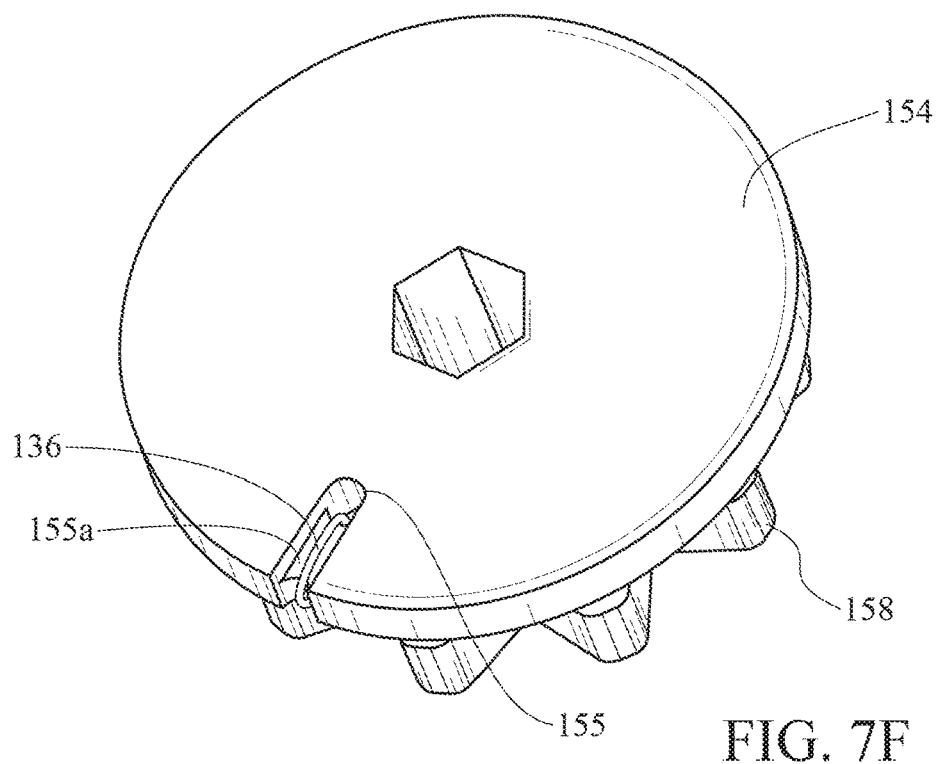

A partially disassembled view of the control handle portion of the steerable catheter device 100 is shown in FIG. 2, and the spool assemblies therein are shown in more detail in FIG. 3. The outer control wheel 110 engages a shaft 114 of, and controls rotation of, an outer spool 112. The outer spool 112 includes a circumferential groove 115 around its outer circumferential surface, which groove 115 receives a tube 117 through which extend the proximal end regions of opposed first and second control fibers 116, 118. The outer spool 112 includes two gear-mounting apertures 121a, 121b, each of which receives and forms a rotation-permitting engagement with the split mounting end 152 of a gear 150. The inner control wheel 130 engages a shaft 134 of, and controls rotation of, an inner spool 132. The inner spool 132 includes a circumferential groove 135 around its outer circumferential surface, which groove 135 receives a tube 137 through which extend the proximal end regions of opposed third and fourth control fibers 136, 138. The proximal end terminus of each control wire (not shown other than by example in FIG. 7E) is secured to a gear. Those of skill in the art will appreciate that rotary actuation of the outer control wheel 110 effects corresponding rotary actuation of the outer spool 112, while rotary actuation of the inner control wheel 130 effects corresponding rotary actuation of the outer spool 132.

Figure 4A:
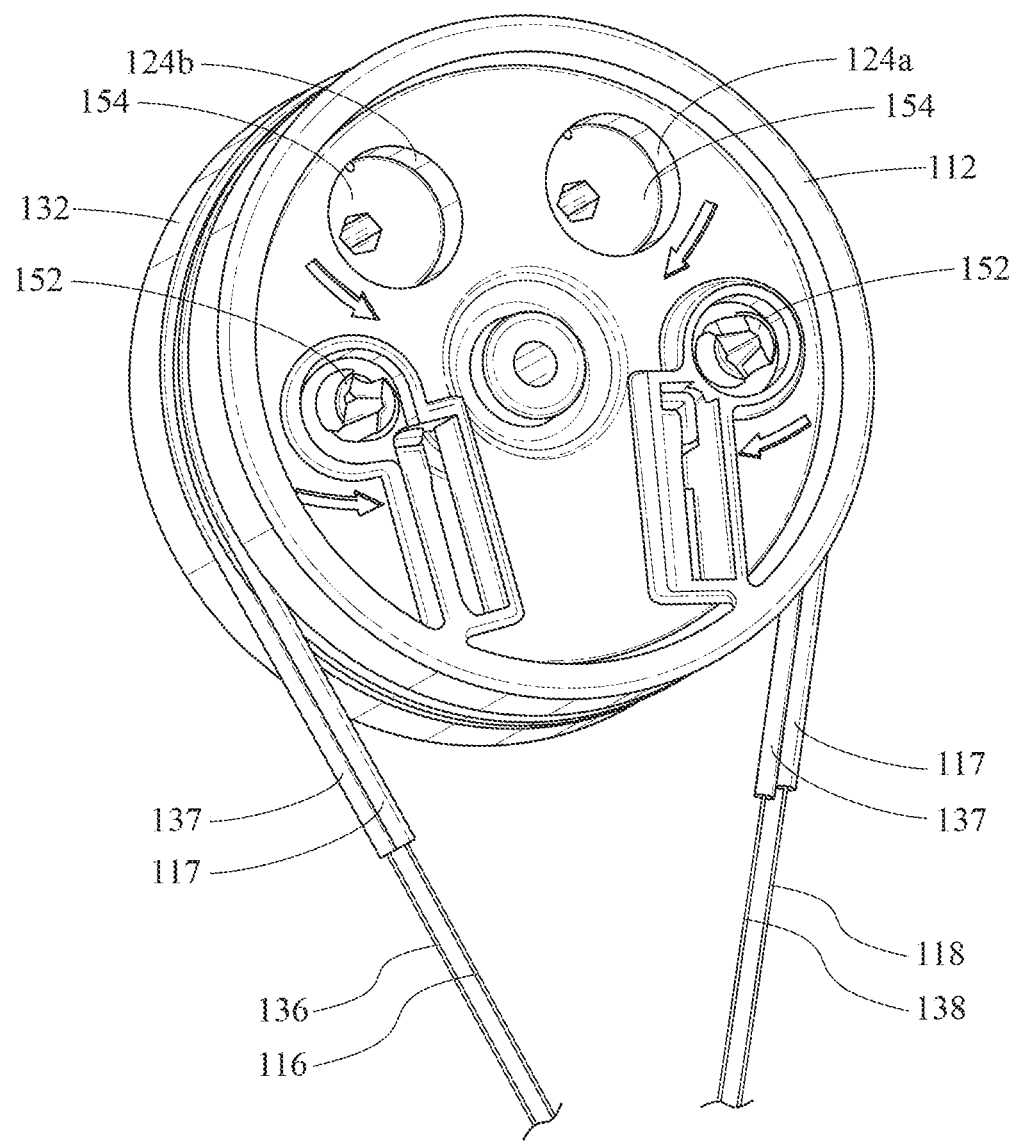
FIGS. 4A-4B depict the spools assembled together with control wires and control wire tubes.

As shown in FIGS. 3 and 4A, the outer spool shaft 114 extends through and beyond a central passage of the inner spool 132 and its shaft 134. In FIG. 3, only two of four actual gears 150 are expressly shown, but it should be appreciated that a four-wire control system will include four gears 150, each securing a proximal end portion of one of those four wires (e.g., 116, 118, 136, 138). More detailed views of the gears 150 are shown in FIGS. 7A-7D. Each of the spools 112, 132 also includes gear-engaging detents, which are depicted here as flexible beams 122a, 122b, 142a, 142b. The outer spool 112 also includes a pair of gear-adjustment access apertures 124a, 124b, which allow access to the gears 150 engaged into the inner spool 132 when the two spools, 112, 132 are rotationally oriented and aligned in a predetermined position as shown, e.g., in FIGS. 3 and 4A. With this structural configuration, a user can access each of the gears 150 to turn it and thereby adjust the slackness and/or tension of a control wire attached to the gear. This ability remains when the spools are assembled together, and when they are engaged to their respective control wheels 110, 130, provided that the spools are aligned in a predetermined manner (required for post-assembly adjustment of the inner spool 132).

Figure 4B:
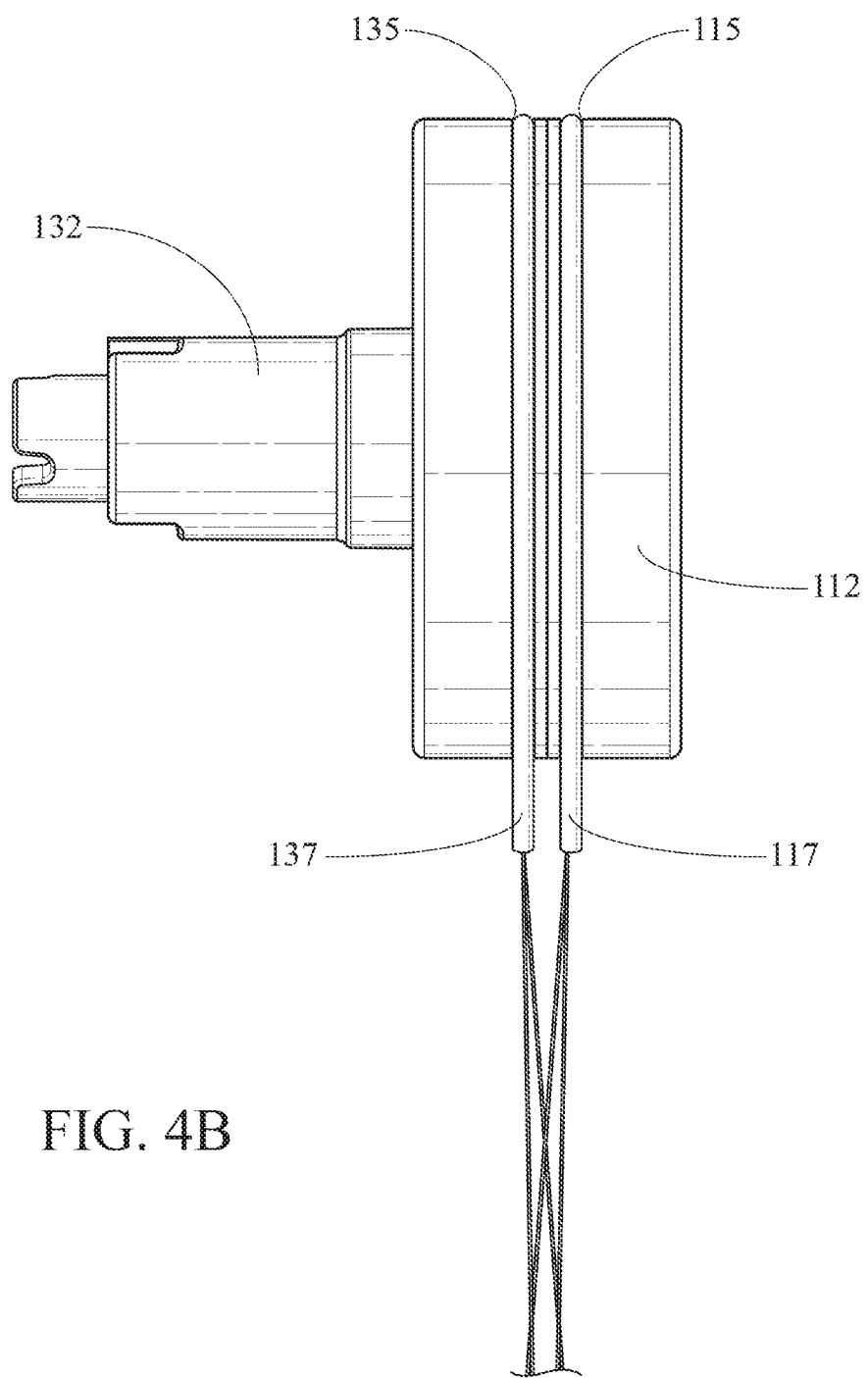

FIGS. 4A-4B show the outer spool 112 rotatably engaged with/through the inner spool 132, where the split mounting end 152 of the gears 150 engaged rotatably into the apertures 121a, 121b of the outer spool are visible. The hex-receiving heads 154 of the gears 150 (that are rotatably engaged into the inner spool 132) are visible through the gear-adjustment access apertures 124a, 124b. The outer spool tube 117 and inner spool tube 137 are shown engaged in their respective grooves 115, 135. Control wires 116, 118 extend from the ends of the outer spool tube 117, and control wires 136, 138 extend from the ends of the inner spool tube 137.

Figure 5A:
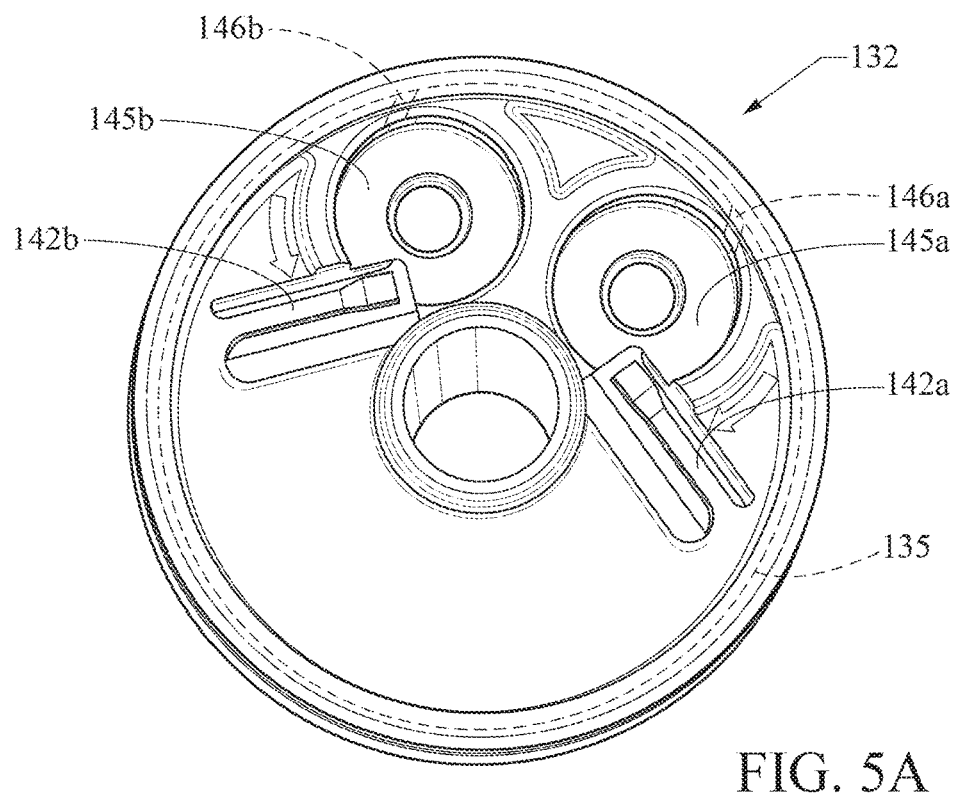
FIGS. 5A and 5B show a face of the inner spool, respectively, without and with a pair of engaged control-wire winding gears.
Figure 5B:
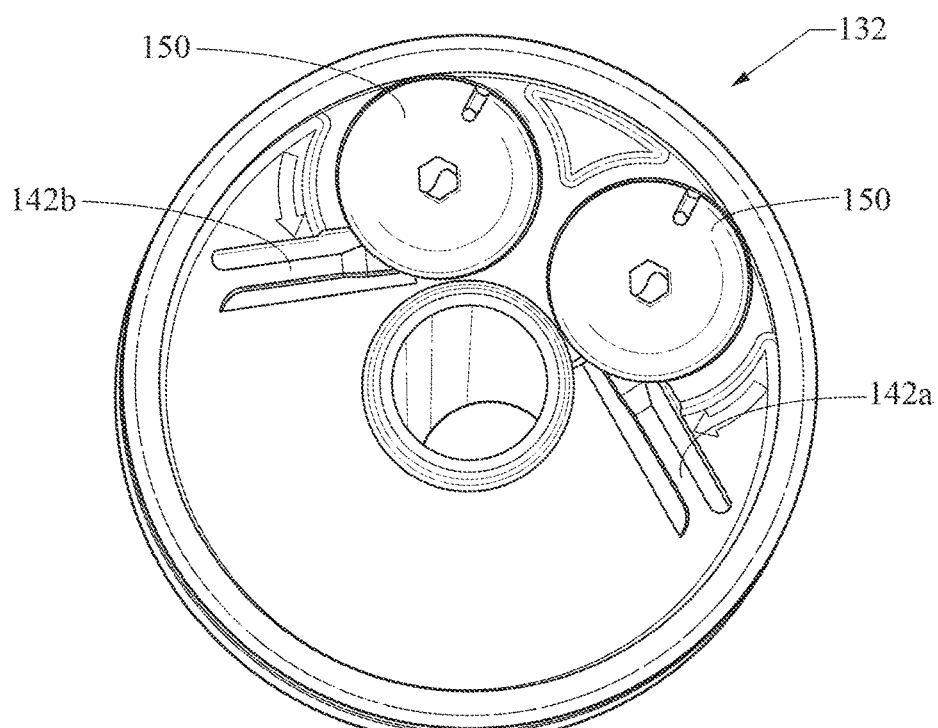
Figure 6A:
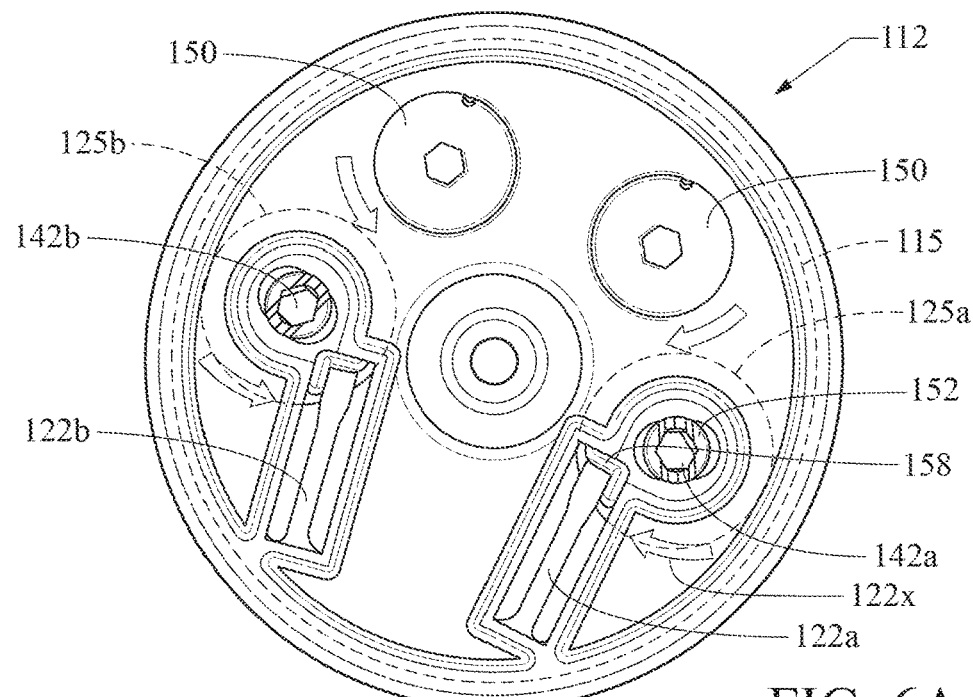
FIG. 6A shows an outer face of the outer spool, assembled to the inner spool (of which portions, including inner spool gears, are partially visible.
Figure 6B:
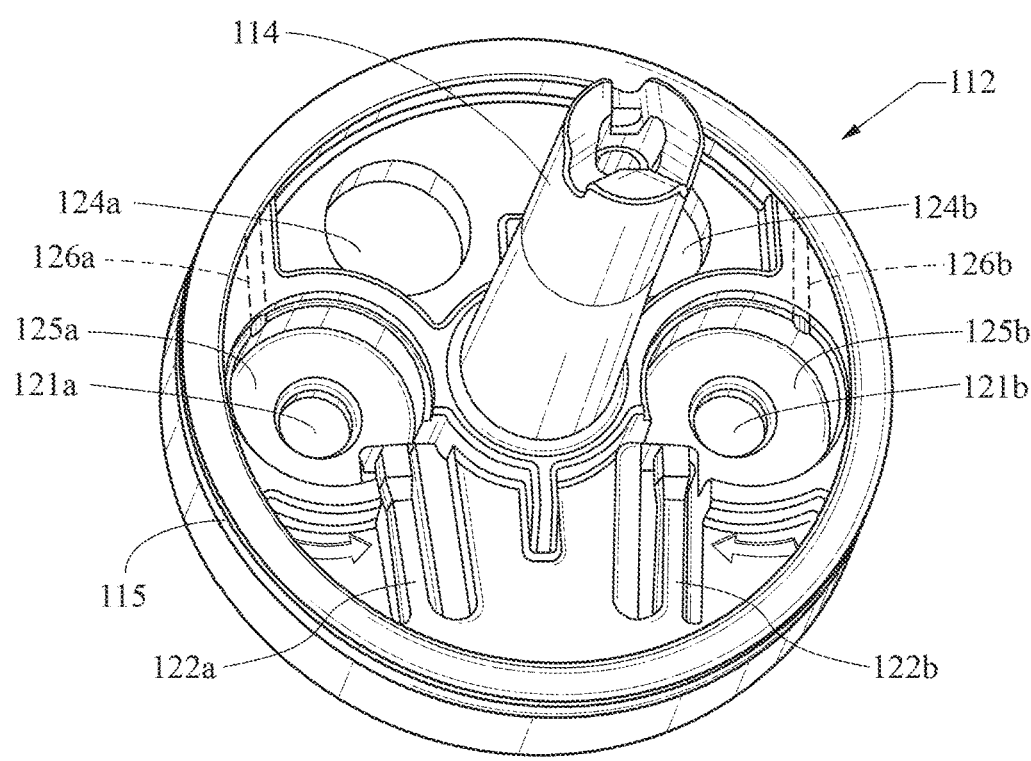
FIG. 6B shows an inner face of the outer spool.

As shown in FIGS. 5A-5B and 6A-6B, respectively, the inner spool 132 and the outer spool 112 each include control wire passages. FIG. 5A shows the outer spool-facing surface of the inner spool 132, and FIG. 5B shows the same surface, with gears 150 mounted therein. For the inner spool 132, a pair of control wire passages 146a, 146b extend from the groove 135 into, respectively, the gear receptacles 145a, 145b. FIG. 6A shows an outward facing surface of the outer spool 112 (including gears engaged into the outer spool 112, with a view through its openings of detents 142a, 142b and of gears engaged into the inner spool 132), and FIG. 6B shows the opposite surface without the gears. For the outer spool 112, a pair of control wire passages 126a, 126b extend from the groove 115 into, respectively, the gear receptacles 125a, 125b. The orientation of each passage is configured to provide a minimal angle relative both to the groove and to the gear receptacle so that when a control wire is directed through the passage and engaged to the gear, there are minimal stress risers that could serve as binding points and/or that could introduce undesirable point stresses to the control wires during device operation. Once assembled to a spool and engaged with a control wire each of the gears rotates in place without moving along or out of a central radial/rotary axis.

FIGS. 7A-7D show four views of the control wire tensioning gear 150. Each gear includes a splayed/split mounting end 152 that is used in a "clip-in" engagement into—and allowing rotation within—gear-mounting apertures (121a, 121b, 141a, 141b). The split mounting end 152 is sufficiently flexible and resilient to engage securely but rotatably within those gear-mounting apertures. Each gear also includes a hex-receiving head 154, shown here as planar and circular, connected with and separated from a gear-toothed disk 158 by a core member, the surface of which forms a control-wire-receiving circumferential groove 156 of the gear 150.

The faces of adjacent gear teeth 158a preferably are oriented about 90° relative to each other and at about 45° relative to a radially central diameter, as shown in the drawings. This construction provides for a firm and secure engagement of the squared off end of a detent between adjacent teeth. As shown, for example, in FIG. 6A, the squared-off end of a detent embodied as a flexible beam 122a is firmly and securely engaged between adjacent gear teeth. Those of skill in the art will appreciate that a hex-head tool (e.g., Allen wrench) can be engaged within the hex-shaped opening of the split mounting end 152 so as to rotate the gear. In FIG. 6A, rotation of the lower-right gear in the clockwise direction indicated by surface marking arrow 122x will deflect the beam 122a and allow the gear to rotate in a controlled manner. With reference to FIG. 6B, it will be appreciated that a control wire passing from the groove 115 through the passage 126a into the gear receptacle 125a can be secured to a gear therein and will be (with said rotation) wound up around the gear to gather slack and adjust tension. In the event that the gear is wound farther than desired, the detent 122a can be deflected to allow the gear to be rotated/released in the opposite direction (thereby reducing tension on the control wire).

With reference to FIG. 6A and FIG. 5B, it should also be appreciated that the detents 142a, 142b and gears of the inner spool 132 can be adjusted when the inner and outer spools are assembled together. The hexagonal apertures of the gear heads 154 can be engaged for wire-tightening/tensioning rotation in the direction shown by the respective surface indicia arrows (on the upper portion of FIG. 6A). And, if there is a desire of a user to counter-rotate either inner spool gear, the inner spool detent 142a, 142b engaged to the gear can be deflected by accessing them through the central opening of the outer surface gears between their respective split mounting ends 152. Preferably, each of the control wires 116, 118, 136, 138 is directed a maximal distance around the spool to which it is engaged, which those of skill in the art will understand to provide a more desirable range of mechanical movement for/of the control wires with regard to controlled deflection of the catheter distal end.

The preferred travel path of each control wire is described with reference to FIGS. 4A, 5A, and 6B. On the outer spool, the control wire 116 is disposed through the longitudinal central lumen of the tube 117 and exits a tube opening (not shown) that is aligned with the control wire passage 126a, through which passage 126a the wire 116 is disposed to engage around a gear rotatably mounted in the gear receptacle 125a. The control wire 118 (a distal end of which preferably is securely fixedly attached in a distal catheter portion, about or exactly 180° opposite of control wire 116) is disposed through the longitudinal central lumen of the tube 117 and exits a tube opening (not shown) that is aligned with the control wire passage 126b, through which passage 126b the wire 118 is disposed to engage around a gear rotatably mounted in the gear receptacle 125b.

On the inner spool, the control wire 136 is disposed through the longitudinal central lumen of the tube 137 and exits a tube opening (not shown) that is aligned with the control wire passage 146a, through which passage 146a the wire 136 is disposed to engage around a gear rotatably mounted in the gear receptacle 145a. The control wire 138 (a distal end of which preferably is securely fixedly attached in a distal catheter portion—not shown, about or exactly 180° opposite of control wire 136) is disposed through the longitudinal central lumen of the tube 137 and exits a tube opening (not shown) that is aligned with the control wire passage 146b, through which passage 146b the wire 138 is disposed to engage around a gear rotatably mounted in the gear receptacle 145b.

Each control wire preferably is securely and permanently attached to a gear 150 in a manner that provides for predictable and desirable performance of the device with regard not only to removal of slack and tensioning during assembly of a steerable catheter device, but also during operation of the device including steering/deflection of the distal catheter portion. In view of the foregoing description, it should be appreciated that, during assembly, a proximal end of the control wire is directed into a gear receptacle via a control wire passage. For the sake of exemplary illustration, reference is made here to FIGS. 6B and 7A-7F. When directed through the control wire passage 126b, a distal end of the control wire 118 (not shown in FIGS. 6B-7D) will traverse the gear receptacle 125b in a position that will align with the groove 156 of a gear 150.

In one preferred embodiment, the control wire will be directed from the groove 156 through a wire-securing fenestration 155 that is open through the gear head 154. From that fenestration 155, the distal end of the wire 118 passes along and within a slot 155a disposed radially in the outward face of the gear head 154, then traverses the thickness of the gear head 154 via a notch 155b (which notch is within the outer circumference of the gear head 154). There, back within the groove 156, the distal end of the wire 118 can be knotted around a less-distal portion of the wire 118, and the knot preferably secured with adhesive (knot not shown, but various knots and adhesives are well-known in the art). It will be appreciated that a couple of turns of the wire around the core within the groove will additionally frictionally secure the wire around the groove, whereupon the split mounting end 152 of the gear can be mounted/"clicked" into the gear-mounting aperture 121b for adjustment to take up slack and tension the wire as described above. Those of skill in the art will appreciate this process with respect to providing secure windability of the control wires relative to each of the four gears in the drawings and this description, which four wires and gears provide for controlled deflection/movement along and between all four transverse axes of the distal catheter end. It is preferable that the control wire be secured around/through the gear head and not through the core/shaft—both for ease of assembly, and also to minimize the stress risers present in the wire along its load-bearing regions during tensioning and operation of the steerable catheter.

Figure 8:
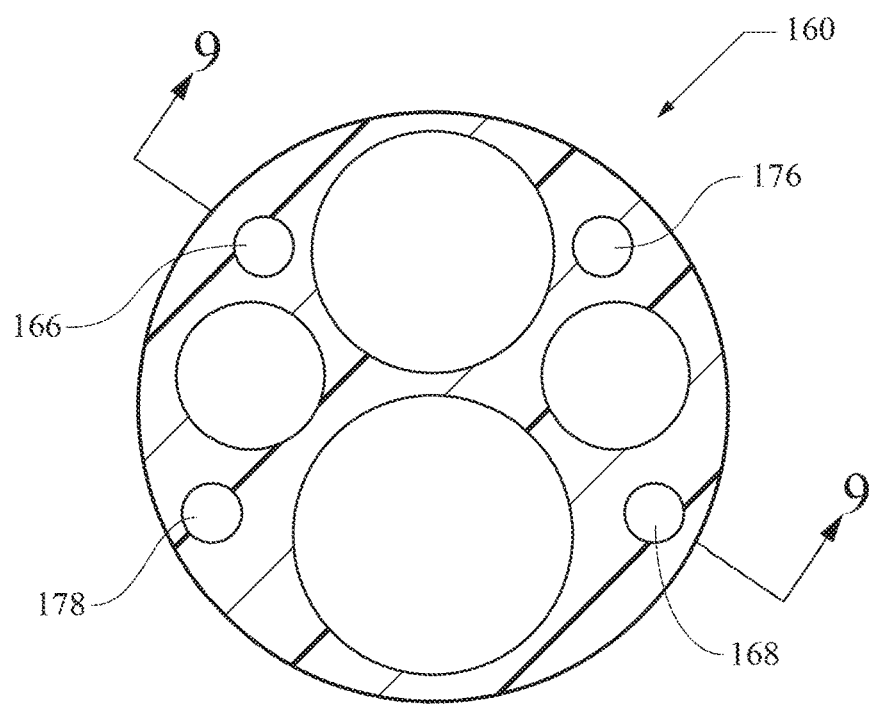
FIG. 8 is a transverse section view taken along line 8-8 of FIG. 1, showing an eight-lumen catheter body.

One of the challenges in constructing a steerable catheter device (including particularly very small-diameter devices, such as a device configured for use as a cholangioscope) is securely and fixedly/permanently attaching control wires within the distal end, which is imperative for predictable and consistent steering performance. With reference to FIG. 1, for such a device, it is preferable that the distal end portion 160, which here includes a distal length to the distalmost end terminus, be controlled finely and accurately by the steering mechanism so as to be able to be oriented in any direction around a 360-degree circle defined generally by a transverse circumference of the catheter body. FIG. 8 shows a transverse section view of the distal end catheter body portion 160 (taken along line 8-8 of FIG. 1).

The catheter body distal portion 160 shown includes eight lumens that extend longitudinally through the catheter body 104, where all of those lumens are at least generally, preferably substantially, or even exactly parallel with each other. The first and second control wire lumens 166, 168 may receive the paired opposite control wires 116, 118, where the first and second lumens are disposed radially 180° opposite each other across a radially off-center longitudinal axis of the catheter body. The third and fourth control wire lumens 176, 178 may receive the paired opposite control wires 136, 138, where the third and fourth lumens also are disposed radially 180° opposite each other across a radially off-center longitudinal axis of the catheter body. As shown, relative to the radially off-center longitudinal axis of the catheter body, the first and fourth lumens, and the second and third lumens each are disposed radially less than 90° from each other, respectively. Other, larger lumens shown may be configured for purposes other than allowing passage of a control wire (e.g., for passage of a wire guide or other accessory, illumination structure, visualization elements/structures, introduction/extraction of fluids, and/or other purposes). In one embodiment, the outer diameter of the distal end portion 160 may be about 4 mm, with the inner diameter of the control wire lumens 166, 168, 176, 178 each being about 0.3 mm, and the inner diameters of the other lumens ranging from about 0.75 mm to about 1.5 mm.

Figure 9:
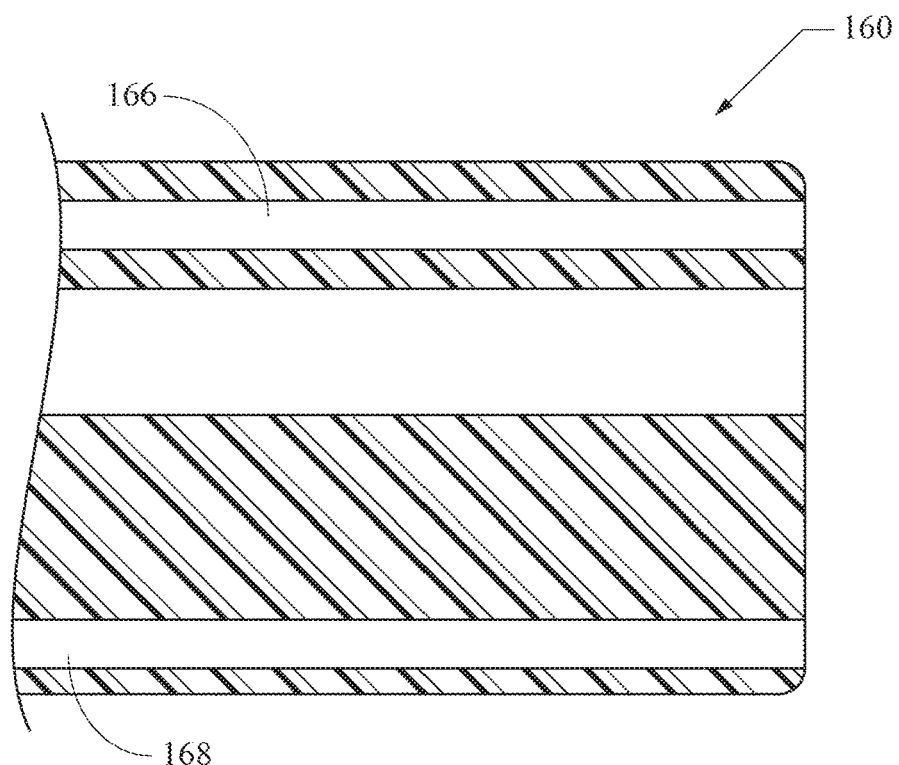
FIGS. 9-9D are longitudinal section views of the distal catheter body, taken along line 9-9 of FIG. 8, with FIGS. 9A-9D showing one (non-limiting) method of securely and permanently affixing a control wire within a distal end of the catheter.

Within each of the control wire lumens, the respective control wire most preferably is free to move longitudinally except for a distalmost length that is securely and fixedly attached within a distalmost terminal length of the corresponding control wire lumen. In some embodiments, at least that a distalmost terminal length of the control wire lumen has a consistent/constant and uniform inner diameter that does not get larger at or near the distalmost terminus of the catheter body. In other embodiments, the distalmost terminal length of the control wire lumen may be slightly but smoothly flared to a larger inner diameter, but without any stepped or sharp transition of diameter. This is more clearly shown in FIG. 9, which is a longitudinal section view of the distal catheter body portion 160 taken along line 9-9 of FIG. 8, crossing through the radially off-center longitudinal axis.

Figure 9A:
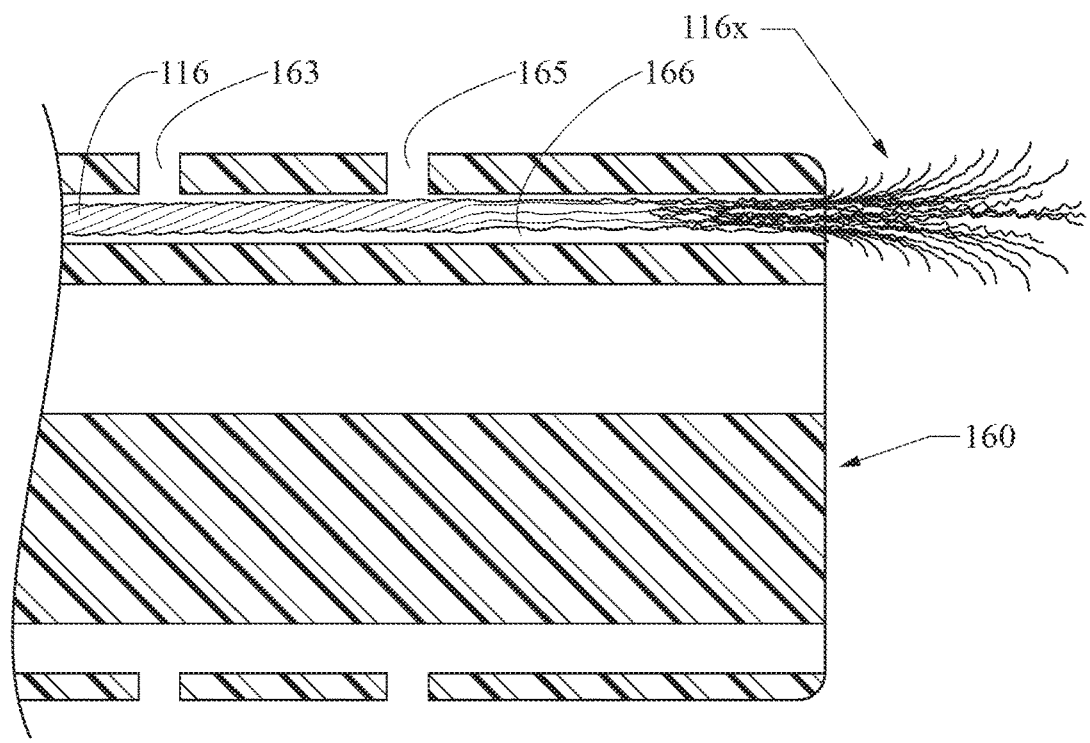

A non-limiting exemplary method of securing a control wire, useful in each of the control wire lumens, is described here with reference to FIGS. 9A-9D. The wire and adhesives are not drawn to scale. As shown in FIG. 9A, a control wire 116 is directed through the control wire lumen 166, leaving a distalmost end terminal length of the control wire outside the distal terminus of the catheter distal end portion 160. A lengthwise portion 116x of the exposed wire is frayed or otherwise at least partially disaggregated. For an UHMWPE fiber, other (e.g., non-UHMWPE) polyethylene fiber, or braided or twisted polymer fiber or yarn, this may be done by gripping and pulling with a tool (e.g., tweezers, pliers, blade edge) along and past the distalmost terminal end of the wire. Control wire comprising another yarn or cable material may be unwound or otherwise disaggregated into a plurality or other multiplicity of component fibers—most preferably without breaking, cutting, or weakening the longitudinal composition of those component fibers.

Figure 9B:
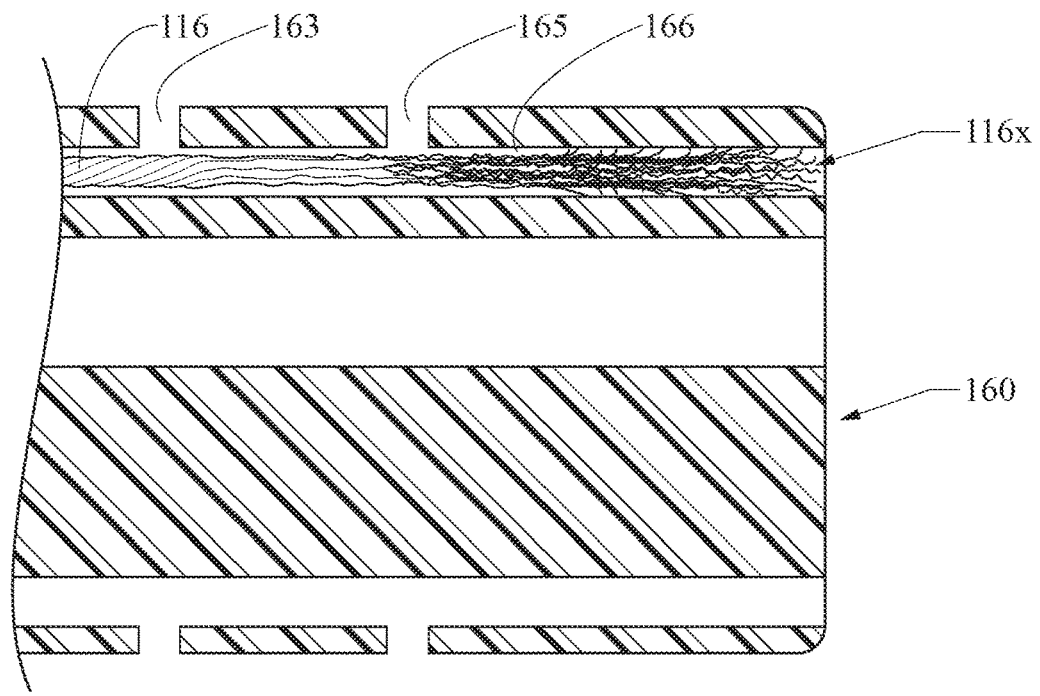
Figure 9C:
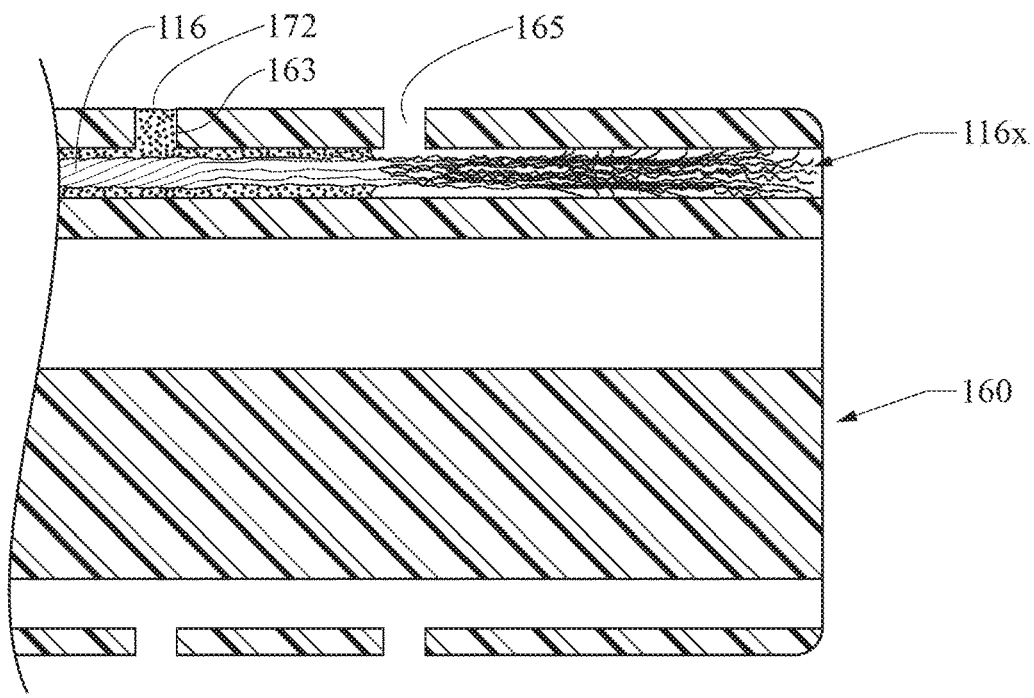
Figure 9D:
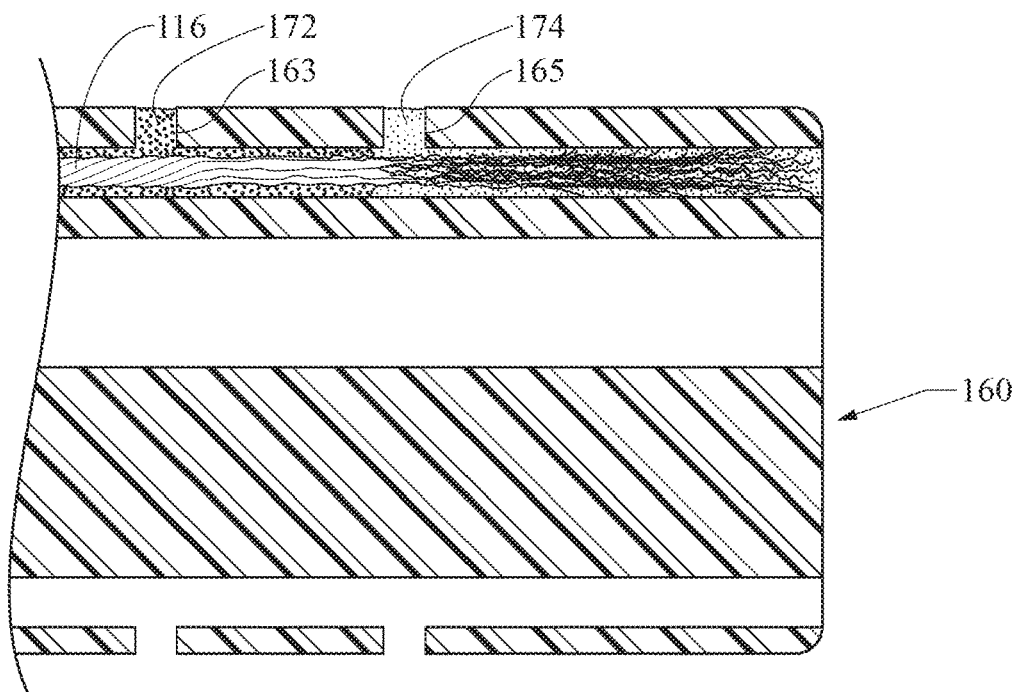

A pair of side holes 163, 165 is also shown in FIGS. 9A-9D. These holes are configured for introducing flowable adhesive into the lumen 166. As shown in FIG. 9B, the wire 116 is drawn into the lumen 166—preferably so that the frayed/disaggregated distal ends are at least generally aligned with or flush with the distal terminal catheter end. Then, as shown in FIG. 9C a more-viscous adhesive 172 is wicked or otherwise directed through the more-proximal hole 163 into the lumen 166 and around the wire 116, where the adhesive generally surrounds and may at least partially permeate the wire (particularly for embodiments where the frayed/disaggregated distal length 116x extends proximally to or past the more-proximal hole 163). The introduction of adhesive, whether by wicking, injection, or other means may include some capillary action as well, thereby allowing cross-sectional filling of the lumen 166 through and around the wire 116 and its frayed portion. Most preferably, the more-viscous adhesive 172 does not block the more-distal side hole 165. As shown in FIG. 9D, a less-viscous adhesive 174 is wicked or otherwise directed through the more-distal hole 165 into the lumen 166 and around the wire, where the adhesive generally surrounds and may at least partially permeate the wire and—as thoroughly as possible—permeates between, intersperses, and engages with the frayed or otherwise at least partially disaggregated elements of the distalmost terminal wire end 116x. Thereafter, any excess adhesive is cleaned off and the adhesive is allowed to cure and set in a manner that permanently fixes and secures the wire 116 within the distal length of the lumen 166. More proximally, the wire preferably is at least generally freely movable within the lumen, and its opposite (proximal) end may be secured within a control handle as described above, or by other means known or developed in the art.

Those of skill in the art will appreciate that a variety of different particular adhesives may be used in view of the presently disclosed novel structures and methods. The particular choice(s) of adhesive(s) may vary in keeping with the materials used for the catheter and the wire(s), as well as with regard to the dimensions and particular application/environment for which a given steerable catheter is configured. One exemplary embodiment of the present disclosure includes distalmost end terminal catheter length 160 extruded as a 50/50 blend of PEBAX-7233 and Nylon-12. With this material, and with a 4×-50 Denier ultra-high tenacity polyethylene braid (described above, having its distalmost terminal end length 116x teased out and frayed), one example of a proximal-use, more-viscous adhesive may be a cyanoacrylate of about 100 cP (e.g., Loctite™ 401), and one example of a distal-use, less-viscous adhesive may be a cyanoacrylate of about 3 cP (e.g., Loctite™ 4014).

Other effective adhesives may include UV-curable and/or other light-curable adhesives. The viscosity of the adhesives may be selected with particular reference to the absolute and relative sizes of the wire lumen(s) and the wire(s). The materials and sizes, particularly of the wire(s) will be selected to transfer desired/needed force without breaking or stretching, without binding in the lumen(s), and also remaining small enough to keep the overall device of a desired size. Also, the catheter may include one or more metallic and/or polymeric reinforcing members (e.g., within the catheter wall, on the catheter wall exterior), but the control wires are not directly attached to any such members by the adhesive nor by other engagement. In preferred embodiments, the control wires exclude any sheath member, being constructed of materials that provide desired strength and limited elasticity in the very small diameters contemplated for the device embodiments described herein.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. References herein to any industry standards (e.g., ASTM standards, and product identifiers such as particular polymers, as well as any trademarks) are defined as complying with the currently published standards and corresponding quantitatively and qualitatively defined specifications as of the original filing date of this disclosure unless expressly otherwise defined herein. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

I claim:

1. A secure attachment of a wire within a steerable catheter comprising:
    an elongate catheter body including
        a proximal end, a distal end, and an intermediate catheter body length therebetween;
        at least a first catheter lumen extending longitudinally through the catheter body;
    at least a first elongate wire disposed longitudinally through the first catheter lumen;
    a first adhesive having a first viscosity, the first adhesive disposed substantially within, and securing the wire to, the first catheter lumen, where at least a lengthwise portion of the wire is frayed or otherwise at least partially disaggregated.

2. The secure attachment of claim 1, further comprising a second adhesive disposed substantially within, and securing the wire to, the first catheter lumen, where the second adhesive has a second viscosity different than the first viscosity.

3. The secure attachment of claim 1, further comprising a first side hole providing fluid communication between the at least a first catheter lumen and an exterior of the catheter body, which first side hole extends through the catheter body.

4. The secure attachment of claim 3, further comprising a second side hole providing fluid communication between the at least a first catheter lumen and the exterior of the catheter body, which second side hole extends through the catheter body in a location distal of the first side hole.

5. The secure attachment of claim 4, where the first adhesive having a first viscosity is disposed adjacent to, and in contact with, the first side hole.

6. The secure attachment of claim 4, where the first adhesive having a first viscosity is further disposed proximal of the first side hole.

7. The secure attachment of claim 4, further comprising a second adhesive disposed substantially within, and securing the wire to, the at least a first catheter lumen, where the second adhesive has a second viscosity that is less than the first viscosity, and where the first adhesive is disposed proximal of the second adhesive.

8. The secure attachment of claim 4,
    further comprising a second hole through the catheter body in fluid communication with the at least a first catheter lumen.

9. The secure attachment of claim 8, further comprising a second adhesive disposed substantially within, and securing the wire to, the at least a first catheter lumen, where the second adhesive has a second viscosity that is less than the first viscosity, and where the first adhesive is disposed proximal of the second adhesive.

10. The secure attachment of claim 9, where the second adhesive is disposed at least in a catheter lumen region distal of the second hole.

11. A method of forming the secure attachment of claim 9, said method comprising steps of:
    directing a distal lengthwise portion of the wire into a distal end of the at least a first catheter lumen where a distalmost terminal end of the wire is frayed or otherwise at least partially disaggregated, and where said distalmost terminal end is within or immediately adjacent to a distalmost end terminal length of the at least a first catheter lumen;

directing the first, more viscous, adhesive through the first hole into the at least a first catheter lumen in a manner that attaches and secures the wire within the at least a first catheter lumen, without blocking the second hole;

directing the second, less viscous, adhesive through the second hole in a manner that intersperses with and securely engages the frayed or otherwise at least partially disaggregated distalmost portion of the wire within the distalmost end terminal length of the at least a first catheter lumen.

12. The secure attachment of claim 9, where the at least a first catheter lumen includes a constant inner lumen diameter along a distalmost end terminal length of the at least a first lumen within which lumen length is disposed both the second adhesive and a distalmost terminal end of the at least a lengthwise portion of the wire contacting the second adhesive.

13. A steerable catheter comprising:
an elongate catheter body including a distal end, with at least a first catheter lumen extending longitudinally through, and open to, the distal end;
at least a first elongate wire disposed longitudinally through the at least a first catheter lumen;
a first adhesive having a first viscosity, the first adhesive disposed substantially within, and securing the wire to, the at least a first catheter lumen; and
a second adhesive having a second viscosity different than the first viscosity—disposed substantially within, and securing the wire to, the at least a first catheter lumen, distal of the first adhesive where at least a lengthwise portion of the wire contacting the second adhesive is frayed or otherwise at least partially disaggregated.

14. The steerable catheter of claim 13, further comprising at least one visualization element disposed near the distal end of the catheter body.

15. The steerable catheter of claim 13, further comprising at least a second catheter lumen extending longitudinally through, and open to, the distal end, where said second catheter lumen is at least generally parallel with the first catheter lumen and is disposed radially 180° opposite the first catheter lumen across a radially off-center longitudinal axis of the catheter body, and where a second elongate wire is disposed longitudinally through, and secured by at least one adhesive within, the second catheter lumen.

16. The steerable catheter of claim 15, further comprising a third catheter lumen and a fourth catheter lumen,
where each of the third catheter lumen and the fourth catheter lumen is at least generally parallel with the first catheter lumen;
where each of the fourth catheter lumen and the third catheter lumen are disposed radially less than 90° from, respectively, the first catheter lumen and from the second catheter lumen, relative to the radially off-center longitudinal axis of the catheter body;
where a third elongate wire is disposed longitudinally through, and secured by at least one adhesive within, the third catheter lumen; and
where a fourth elongate wire is disposed longitudinally through, and secured by at least one adhesive within, the fourth catheter lumen.

17. The steerable catheter of claim 16, where the distal end of the catheter is configured to be deflected in a controlled manner by simultaneously increasing and decreasing pulling force, respectively, upon the first elongate wire and second elongate wire and/or the third elongate wire and fourth elongate wire.

18. The steerable catheter of claim 16, where each of the catheter lumens has a uniform consistent inner diameter along at least a distalmost terminal end length, within which length each of the elongate wires is disposed and secured.

19. The steerable catheter of claim 13, where the at least a first catheter lumen has a uniform consistent inner diameter along at least a distalmost terminal end length of the lumen, within which lumen length at least a first elongate wire is disposed and secured by the first adhesive and the second adhesive.

20. A method of forming the secure attachment of claim 19, said method comprising steps of:
directing a distal lengthwise portion of the wire into a distal end of the catheter lumen where a distalmost terminal end of the wire is frayed or otherwise at least partially disaggregated, and where said distalmost terminal end is within or immediately adjacent to the distalmost end terminal length of the catheter lumen;
directing the first, more viscous, adhesive through a first hole into the catheter lumen in a manner that attaches and secures the wire within the catheter lumen, without blocking a second hole;
directing the second, less viscous, adhesive through the second hole in a manner that intersperses with and engages the frayed or otherwise at least partially disaggregated distalmost terminal end of the wire within the distalmost end terminal length of the catheter lumen.

* * * * *